(12) United States Patent
Sabczynski et al.

(10) Patent No.: US 7,729,743 B2
(45) Date of Patent: Jun. 1, 2010

(54) METHOD AND ARRANGEMENT FOR TRACKING A MEDICAL INSTRUMENT

(75) Inventors: Jörg Sabczynski, Norderstedt (DE); Volker Rasche, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 548 days.

(21) Appl. No.: 10/541,624

(22) PCT Filed: Dec. 19, 2003

(86) PCT No.: PCT/IB03/06233

§ 371 (c)(1),
(2), (4) Date: Jul. 6, 2005

(87) PCT Pub. No.: WO2004/060157

PCT Pub. Date: Jul. 22, 2004

(65) Prior Publication Data
US 2006/0173287 A1 Aug. 3, 2006

(30) Foreign Application Priority Data
Jan. 7, 2003 (EP) .................................. 03100011

(51) Int. Cl.
*A61B 8/00* (2006.01)
*G01N 23/00* (2006.01)

(52) U.S. Cl. .................. 600/424; 600/416; 600/428; 600/437; 378/82

(58) Field of Classification Search .............. 600/462, 600/424, 428, 416, 425; 378/62
See application file for complete search history.

(56) References Cited

U.S. PATENT DOCUMENTS

| 5,265,610 | A | 11/1993 | Darrow |
| 5,577,502 | A | 11/1996 | Darrow et al. |
| 5,930,329 | A * | 7/1999 | Navab ..................... 378/98.12 |
| 6,233,476 | B1 * | 5/2001 | Strommer et al. ........... 600/424 |
| 6,246,898 | B1 | 6/2001 | Vesely et al. |

(Continued)

FOREIGN PATENT DOCUMENTS

DE        40 37 586 A1    5/1992

(Continued)

OTHER PUBLICATIONS

Wang, Yi, et al.; Respiratory Motion of the Heart: Kinematics and the Implication for the Spatial Resolution in Coronary Imaging; 1995; MRM; 33:713-719.

*Primary Examiner*—Eric F Winakur
*Assistant Examiner*—Helene Bor

(57) ABSTRACT

The invention relates to a method and an arrangement for the intravascular or intracardial navigation of a catheter (5). Using an X-ray fluoroscopy device (1), firstly an image database of 2D images is generated, where at the same time as each 2D image (I) is taken the associated heartbeat phase is recorded using an ECG (8). During the catheter intervention, the position of the catheter (5) is measured by means of a position measurement unit (6), and at the same time the ECG and preferably also a signal that is dependent on the breathing movement are recorded. The current spatial position of the catheter (5) that is measured is then assigned the 2D image of the image database which corresponds in terms of the heartbeat phase and also possibly in terms of the breathing phase, on which image the position of the catheter can be represented.

11 Claims, 1 Drawing Sheet

U.S. PATENT DOCUMENTS

Figure 1:
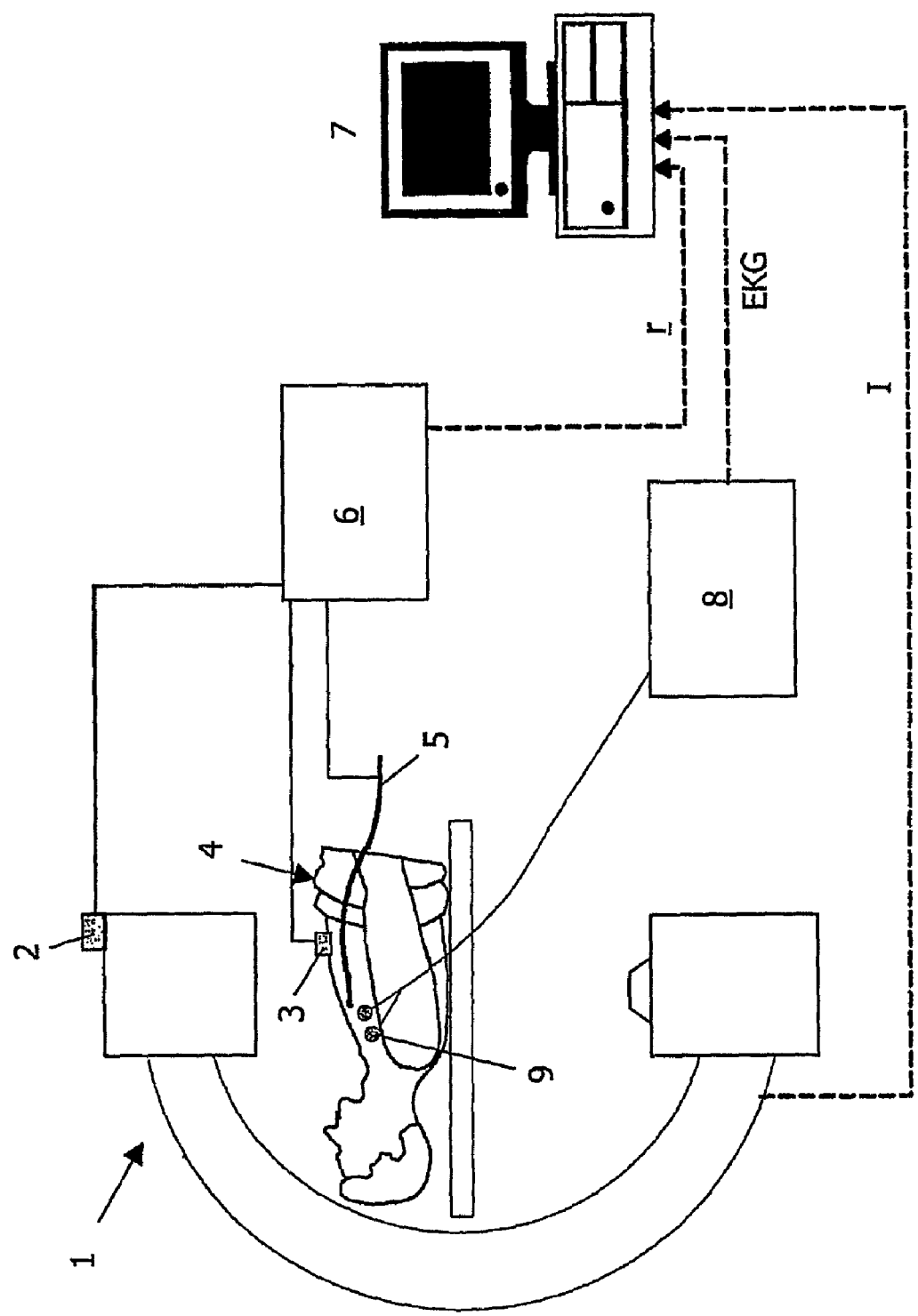

| | | |
|---|---|---|
| 6,379,043 B1 | 4/2002 | Zylka et al. |
| 6,471,399 B1 | 10/2002 | Zylka et al. |
| 6,473,635 B1 | 10/2002 | Rasche |
| 6,895,267 B2 * | 5/2005 | Panescu et al. ............... 600/424 |
| 2001/0031919 A1 | 10/2001 | Strommer |
| 2001/0052899 A1 * | 12/2001 | Simpson et al. ............. 345/419 |
| 2002/0026115 A1 * | 2/2002 | Nehrke et al. ............... 600/410 |
| 2002/0049375 A1 * | 4/2002 | Strommer et al. ........... 600/407 |
| 2003/0073900 A1 * | 4/2003 | Senarith et al. ............. 600/424 |
| 2003/0088179 A1 * | 5/2003 | Seeley et al. ................ 600/424 |
| 2003/0187358 A1 * | 10/2003 | Okerlund et al. ............ 600/443 |
| 2004/0006268 A1 * | 1/2004 | Gilboa et al. ............... 600/424 |
| 2004/0059217 A1 * | 3/2004 | Kessman et al. ............ 600/424 |
| 2004/0097806 A1 * | 5/2004 | Hunter et al. ............... 600/434 |
| 2004/0143184 A1 * | 7/2004 | Kienzle, III ................. 600/424 |
| 2004/0267113 A1 * | 12/2004 | Thomson .................... 600/427 |
| 2005/0080328 A1 * | 4/2005 | Vass et al. ................... 600/407 |
| 2005/0085715 A1 * | 4/2005 | Dukesherer et al. ......... 600/424 |
| 2005/0096589 A1 * | 5/2005 | Shachar .................. 604/95.01 |
| 2005/0201510 A1 * | 9/2005 | Mostafavi ...................... 378/8 |
| 2006/0285738 A1 * | 12/2006 | Boese et al. ................ 382/131 |

FOREIGN PATENT DOCUMENTS

| | | |
|---|---|---|
| DE | 199 46 948 A1 | 4/2001 |
| EP | 0 531 081 A1 | 3/1993 |
| WO | WO 99/43253 A1 | 9/1999 |
| WO | WO 00/10456 A1 | 3/2000 |

* cited by examiner

METHOD AND ARRANGEMENT FOR TRACKING A MEDICAL INSTRUMENT

The invention relates to a method of tracking a medical instrument that is inserted into the body of a patient, and to an arrangement that is suitable for carrying out the method.

An arrangement and a method of the type mentioned above are known from DE 199 46 948 A1. In said document, prior to a catheter investigation, an image database having a number of three-dimensional images of a periodically moving organ of the body, such as for example of the heart, is generated, where a movement signal of the organ of the body is recorded at the same time as the images are taken. The movement signal may be, in particular, an electrocardiogram (ECG) and/or a breathing movement signal. During the subsequent medical intervention, the spatial position of the instrument, and also of a reference probe, is determined by a position measurement unit, and at the same time the movement signal is recorded. Using the movement signal, it is then possible for the 3D image that corresponds in terms of the movement phase of the organ of the body to be selected from the image database. Using the position of the reference probe, which is known in this 3D image, it is then possible to determine the current spatial position of the instrument relative to the 3D image, and to represent it, for example, superposed on the 3D image. One disadvantage of the known method is the high expenditure associated therewith. For instance, the three-dimensional images of the organ of the body first have to be produced using X-ray computer tomography or magnetic resonance imaging, and this does not only take a great deal of time but also greatly modifies the conventional working procedures of a catheter laboratory, since the necessary imaging methods are not available in the catheter laboratory and thus the taking of the images requires an additional time-intensive step. Furthermore, the time-intensive 3D imaging methods generally do not permit real-time updating of the 3D image during the intervention.

In the light of this, it is an object of the invention to simplify the tracking of the position of an instrument, so that it can be integrated more easily with the working procedure of an investigation and preferably permits real-time updating of the images during the intervention.

This object is achieved by a method having the features of claim 1 and by an arrangement having the features of claim 11. Advantageous refinements are given in the subclaims.

The method according to the invention for tracking an instrument that is inserted into the body of a patient, such as a catheter or catheter tip for example, comprises the following steps of:

a) Detection of a movement signal which represents the movement phases of a periodic internal movement of the body. Significant examples of a periodic internal movement of the body are the heartbeat and breathing.

b) Generation of 2D images of a patient body volume of interest, and storage of the 2D images in an image database, where the associated imaging parameters (e.g. projection direction, etc.) and the associated movement phase (in the simplest case directly expressed by the movement signal) are stored together with each 2D image during the taking of the 2D image.

c) Measurement of the spatial position of the instrument and optionally also measurement of the spatial position of at least one reference probe, where the reference probe can be fitted in particular externally on the body of the patient and/or on a medical instrument, or can be fitted inside the patient using a reference catheter or another medical instrument.

d) Selection of at least one 2D image from the image database, which 2D image corresponds in terms of its associated movement phase to the movement phase at the time when the spatial position of the instrument was determined in step c).

e) Determination of the position of the instrument on the 2D image selected in step d).

The method has the advantage that the movement of the instrument is tracked using 2D images, which are produced anyway during the conventional procedure of medical (catheter) investigations. It is therefore seldom necessary to use additional equipment. On account of the simultaneous storage of imaging parameters, movement phases and 2D images in the image database, it is possible, during an operative intervention that is in progress, to represent the current spatial position of the instrument on that 2D image from the image database which corresponds to the current movement phase. Displacements and changes in shape of organs of the body on account of periodic internal movements can in this way be taken into consideration or compensated for. Furthermore, movements of the patient as a whole or of the table on which the patient is lying can also be taken into consideration or compensated for.

An electrocardiogram and/or a breathing movement signal that is dependent on the breathing movement of the patient is preferably detected as a movement signal. Using these signals, it is possible to detect the most significant periodic internal movements in the body of a patient and thus to take these into consideration when determining the position of an instrument.

The position of the instrument which is determined in step e) is preferably represented superposed on the 2D images selected in step d). This makes it possible for the investigating physician to track the movement of the instrument directly on the 2D images.

According to a specific refinement of the method, only 2D images from a single movement phase are made available for selection from the image database in step d). This may in particular mean that the image database may even contain just a single 2D image. In this case, step d) of the method is reduced to ascertaining whether or not the only "selectable" movement phase corresponds to the movement phase of the current spatial position of the instrument. If the movement phases correspond to one another, the assignment can take place; otherwise, it must not take place. In this way, it is possible to reduce the representation frequency of the superposed representation of the instrument position and of the selected 2D image, and so an update of the current instrument position will only be represented when the movement phase thereof corresponds to the predefined movement phase of the 2D image. If the heartbeat is used as a basis for the periodic movement, the predefined 2D image can for example correspond to the end-systoles of the heartbeat, so that the superposed representation of the instrument on the 2D image is only refreshed at these points in the cardiac cycle. The computational outlay for the method can thereby be considerably reduced. By always using the same 2D image, a steady-state image background is established, and this facilitates visual tracking of the instrument.

According to another development of the method, step b) on the one hand (generation of 2D images for the image database) and steps c), d), e) on the other hand (measurement of the spatial position of the instrument; selection of at least one corresponding 2D image; determination of the position in the image) are carried out a number of times and in varying order. This means, in particular, that 2D images can be generated even while the operative intervention is in progress, and this ensures that the image database which is used is always up-to-date.

Preferably, the image database contains 2D images from various projection directions. As a result, it is possible to represent the current spatial position of the instrument on various 2D images in parallel, or to select the best suited 2D image from a number of 2D images from a movement phase.

The 2D images are advantageously generated by means of X-radiation and/or ultrasound, so that the apparatus that is conventionally present during a catheter investigation can be used to produce them.

According to a development of the method, at least one reference probe is fitted on a movable X-ray device which is provided for generating the 2D images. The spatial position of the reference probe is then measured, according to steps b) and c) of the method, in parallel with the generation of the 2D images and with the determination of the spatial position of the instrument. Knowing the spatial position of the reference probe on the X-ray device makes it possible to determine the projection direction from the location of the X-ray device, without any additional apparatus being required. If another reference probe is additionally used on the patient, the projection direction can also be determined with respect to the patient.

Furthermore, using movement models of the body, it is possible to compensate for the breathing movement on the basis of the measured breathing positions.

The invention furthermore relates to an arrangement for tracking an instrument that is inserted into the body of a patient, which comprises the following elements:

a) A device for generating 2D images of a body volume of interest.

b) A unit for determining the set imaging parameters of the device.

c) A signal measurement unit for detecting a movement signal which represents the movement phases of a periodic internal movement of the body. As mentioned above, the internal movement of the body may in particular be the heartbeat and/or the breathing.

d) A storage unit for storing an image database of 2D images of the body volume together with the imaging parameters and the movement phases which belong to the respective 2D image.

e) A position measurement unit for measuring the spatial position of the instrument that is inserted into the body and optionally of at least one reference probe. The position measurement unit may in particular comprise a transmitter for transmitting (modulated) electromagnetic fields and also a receiver for receiving these fields.

f) A control and computation unit for selecting at least one 2D image from the image database, which 2D image corresponds in terms of its associated movement phase to the movement phase belonging to the spatial position of the instrument, and for determining the position of the instrument on the selected 2D image.

Using the described arrangement, it is possible for the above-described method to be carried out so that its advantages can be achieved. In particular, it is important that the arrangement is compatible with a device such as is present as standard in conventional catheter investigations. In order to be able to represent the position of an instrument on the 2D imaged generated hereby, the arrangement comprises a unit for determining the set imaging parameters of the device. Knowledge thereof makes it possible subsequently to convert the measured spatial position of the instrument into a position on the selected 2D image.

Preferably, the arrangement is designed such that it is suitable for carrying out one or more variants of the method of the type described above. Thus, the signal measurement unit may in particular have means for measuring an electrocardiogram and/or for measuring the breathing movement of the patient. Furthermore, the device may in particular be an X-ray apparatus.

The invention will be further described with reference to examples of embodiments shown in the drawings to which, however, the invention is not restricted. The single FIGURE schematically shows the components of an arrangement according to the invention.

Intravascular interventions are conventionally carried out in a catheter laboratory. Here, the operation field is observed fluoroscopically using an X-ray apparatus 1 fitted on a C-arm. In coronary vessel disorders, a contrasting agent is conventionally applied locally, in order to show the vessel profile on the fluoroscopic image. In the course of therapeutic methods, such as a PTCA (Percutaneous Transluminal Coronary Angioplasty) for example, a catheter 5 is pushed into the target area, for example a stenosis in the heart of the patient 4, and its position is in turn monitored using X-ray fluoroscopy. This means that X-ray fluoroscopy is used not only to show the anatomy of the patient but also to navigate the catheter to its target area. Therefore, the patient and the staff require additional doses of X-radiation which serve solely for navigation.

The arrangement shown in the FIGURE allows, using the existing imaging apparatus of a catheter laboratory, navigation of the catheter 5 during cardiac or other intravascular interventions with a reduced amount of X-radiation. The overall system consists of a position measurement unit 6, such as for example an electromagnetic position measurement system (cf. DE 199 46 948 A1), which allows determination of the spatial position of the tip of the catheter 5 and also of a reference probe 3 on the patient 4 or of a reference probe 2 on the X-ray device 1 in a stationary coordinate system;

a medical workstation (computer) 7, which receives the positions r determined by the position measurement unit 6, the electrocardiogram ECG from the ECG system 8, and the X-ray images I from the X-ray device 1;

an X-ray fluoroscopy device 1 which is tracked and calibrated in terms of its setting by a reference probe 2;

a tracked catheter 5 or guidewire;

reference probes 3 on or in the patient;

an ECG system 8 for taking an electrocardiogram using electrodes 9 attached to the patient.

Using such an arrangement, it is possible to navigate the catheter 5 in accordance with the following steps:

1. Preoperative Calibration Phase:

During a calibration procedure, the imaging parameters of the fluoroscopic system 1 are determined. This calibration need be carried out only once, for example at the manufacturer's premises or during installation of the system 1 (see, for example, U.S. Pat. No. 6,379,043, U.S. Pat. No. 6,471,399).

2. Image Generation Phase During the Intervention:

2.1. Preparation: Preparation of the patient 4 including attachment of the ECG electrodes 9; fitting of the reference probes 3 for position tracking on the patient 4 (in the case of cardiac interventions on the thorax).

2.2. Data gathering:

2.2.1. An X-ray image I or an image sequence is generated using the X-ray fluoroscopy system 1, where the anatomy of interest of the patient 4 is visible on the images.

2.2.2. For each image of the taken image sequence, additional information is recorded at the time it was taken, specifically, in particular, the current position of the C-arm of the X-ray fluoroscopy system 1, the current position of the reference probe(s) 3 on the patient and the associated ECG phase. The images and the aforesaid additional information form multimodal data.

2.3. Data transmission: All images I and the corresponding data are transmitted to the medical workstation 7. Thus, all information required for navigation is present on the workstation 7.

2.4. If desired or necessary, the imaging steps 2.2. and 2.3. can be repeated for other orientations of the C-arm of the X-ray device 1.

3. Navigation During the Intervention:

During the intervention, the position-tracked catheter 5 or guidewire can be navigated without the need for further X-ray images:

3.1. Position measurement: First, the position of the patient 4 and of the catheter 5 is measured using the position measurement system 6.

3.2. Data gathering: Simultaneously, the ECG phase is measured using the ECG system 8.

3.3. Image selection: Based on the ECG phase, the corresponding image or the corresponding images from the image database obtained in 2.2. are selected by the workstation 7.

3.4. Graphic superposition: From the available data together with the position of the X-ray device 1, a virtual graphic superposition of the catheter on the selected X-ray image is carried out during the taking of the images, without further images having to be taken by X-ray.

3.5. Repetition: Steps 3.1.-3.4. are carried out continuously.

The arrangement as shown in the FIGURE thus allows very precise intravascular or intracardial navigation on X-ray fluoroscopy images with a reduced amount of X-radiation.

According to a variant of the method, the latter can be carried out with a reduced update frequency. In this case, a reference image is selected from the multimodal data generated in step 2.2. For example, this may be the image from the end systolic phase of the cardiac cycle. Instead of again and again displaying images corresponding to the current ECG phase in steps 3.3. and 3.4., only the aforesaid reference image is used. That is to say that an update of the catheter position in step 3.4. on the reference image is only carried out when the currently measured heartbeat phase corresponds to the heartbeat phase of the reference image (that is to say to the end systolic phase). In this way, the update rate is reduced to one update per cardiac cycle.

According to another development of the method, in step 2.2.2. additionally a breathing sensor is used, in order to measure the current breathing phase of the patient 4. The breathing phase is then stored along with the images I and the ECG phase in the multimodal data. In step 3.2., the breathing phase is likewise measured. In step 3.3., the associated image is then selected on the basis both of the ECG phase and of the breathing phase. The rest of the method then proceeds unchanged. If in phase 2.2. of data gathering not enough data can be obtained, then suitable interpolation methods can be used in order to calculate the superposed catheter position of the image. Furthermore, a movement correction for the breathing movement can be carried out as a result of the fact that the breathing-induced movement of the heart can be compensated for based on the measured breathing position using a movement model of the heart.

Another development of the method comprises mixing the steps of data gathering (2.2.-2.4.) and navigation (3.1.-3.5.) with one another. In this way, it is possible for the fundamental 2D images of the image database to be verified, in whole or in part, in real-time during the intervention, so that the image database that is used can be regularly refreshed in whole or in part.

The invention claimed is:

1. A method of tracking an instrument that is inserted into the body of a patient, the method comprising the steps of:
    a) detecting a movement signal which represents movement phases of a periodic internal movement of the body, wherein the movement signal comprises both (i) an electrocardiogram movement signal and (ii) a breathing movement signal;
    b) generating 2D images of a body volume of interest, and storing each 2D image in an image database together with (i) associated imaging parameters and (ii) an associated movement phase;
    c) measuring (i) a current spatial position of the instrument and (ii) a corresponding movement phase of the periodic internal movement of the body comprising (ii)(a) an electrocardiogram movement signal and (ii)(b) a breathing movement signal;
    d) selecting at least one 2D image from the image database, wherein selecting the at least one 2D image takes place only in response to ascertaining whether (i) the at least one 2D image's associated movement phase corresponds to (ii) the movement phase belonging to the current measured spatial position of the instrument, otherwise the selecting does not take place;
    e) determining the position of the instrument on the at least one selected 2D image, wherein determining the position of the instrument on the at least one selected 2D image includes using interpolation to calculate a superposed position of the instrument on the 2D image, and wherein determining further includes compensating for a breathing-induced movement of a given body part within the body volume of interest based on a measured breathing position using a movement model of the body part; and
    f) superposing the determined position of the instrument on the at least one selected 2D image.

2. A method as claimed in claim 1, wherein, in step d), only 2D images from a single movement phase are available for selection from the image database, wherein selecting further includes ascertaining whether or not the single movement phase corresponds to the movement phase of the current measured spatial position of the instrument, and wherein the determined position of the instrument to be superposed on a display of the at least one selected 2D image will only be represented when the movement phase of the current measured spatial position of the instrument corresponds to the single movement phase of the 2D images.

3. A method as claimed in claim 1, wherein steps b) and c) to e) are carried out a number of times and in varying order.

4. A method as claimed in claim 1, wherein the associated imaging parameters in the image database for corresponding 2D images include various projection directions.

5. A method as claimed in claim 1, wherein the 2D images are generated in step b) by means of X-radiation and/or ultrasound.

6. A method as claimed in claim 1, wherein at least one reference probe is fitted on a movable X-ray device which is provided for generating the 2D images.

7. A method as claimed in claim 1, wherein at least one reference probe is arranged on or in the body of the patient.

8. An arrangement for tracking an instrument that is inserted into the body of a patient, the arrangement comprising:

a) a device for generating 2D images of a body volume of interest;
b) a unit for determining imaging parameters of the 2D image generating device;
c) a signal measurement unit for detecting a movement signal which represents movement phases of a periodic internal movement of the body, wherein the movement signal comprises both (i) an electrocardiogram movement signal and (ii) a breathing movement signal;
d) a storage unit for storing an image database of 2D images of the body volume together with (i) associated imaging parameters and (ii) associated movement phases;
e) a position measurement unit for measuring (i) a current spatial position of the instrument that is inserted into the body and (ii) a corresponding movement phase of the periodic internal movement of the body, the corresponding movement phase including both (ii)(a) an electrocardiogram movement signal and (ii)(b) a breathing movement signal; and
d) a control and computation unit for selecting at least one 2D image from the image database, wherein selecting the at least one 2D image takes place only in response to ascertaining whether (i) the at least one 2D image's associated movement phase corresponds to (ii) the movement phase belonging to the current measured spatial position of the instrument, and for determining a superposed position of the instrument on the at least one selected 2D image, wherein determining the superposed position of the instrument on the at least one selected 2D image includes using interpolation to calculate the superposed position of the instrument on the 2D image, and wherein determining further includes compensating for a breathing-induced movement of a given body part within the body volume of interest based on a measured breathing position using a movement model of the body part.

9. An arrangement as claimed in claim 8, wherein it is designed for carrying out a method compromising:
a) detecting a movement signal which represents movement phases of a periodic internal movement of the body, wherein the movement signal comprises both (i) an electrocardiogram movement signal and (ii) a breathing movement signal;
b) generating 2D images of a body volume of interest, and storing each 2D image in an image database together with (i) associated imaging parameters and (ii) an associated movement phase;
c) measuring (i) a current spatial position of the instrument and (ii) a corresponding movement phase of the periodic internal movement of the body comprising (ii)(a) an electrocardiogram movement signal and (ii)(b) a breathing movement signal;
d) selecting at least one 2D image from the image database, wherein selecting the at least one 2D image takes place only in response to ascertaining whether (i) the at least one 2D image's associated movement phase corresponds to (ii) the movement phase belonging to the current measured spatial position of the instrument, otherwise the selecting does not take place;
e) determining the position of the instrument on the at least one selected 2D image, wherein determining the position of the instrument on the at least one selected 2D image includes using interpolation to calculate a superposed position of the instrument on the 2D image, and wherein determining further includes compensating for a breathing-induced movement of a given body part within the body volume of interest based on a measured breathing position using a movement model of the body part; and
(f) superposing the determined position of the instrument on the at least one selected 2D image.

10. An instrument tracking system for tracking an instrument that is inserted into the body of a patient, the instrument comprising:
a) a means for generating and storing 2D images of a volume of interest in a body prior to insertion of an instrument into the body;
b) a means for measuring movement phases of a periodic internal movement of the body, wherein the periodic internal movement comprises both (i) a cardiac system movement and (ii) a respiratory system movement;
c) a means for correlating said 2D images with said movement phases;
d) a means for tracking (i) a current spatial position of the instrument upon insertion into the body and (ii) a corresponding movement phase of the periodic internal movement of the body comprising (ii)(a) an electrocardiogram movement signal and (ii)(b) a breathing movement signal;
e) a means for selecting a stored 2D image based on real-time measurement of the movement phases, wherein selecting the stored 2D image takes place only in response to ascertaining whether (i) the stored 2D image's associated movement phase corresponds to (ii) the movement phase belonging to the tracked current spatial position of the instrument;
f) a means for determining a superposed position of the instrument on the selected stored 2D image, wherein determining the superposed position of the instrument on the selected stored 2D image includes using interpolation to calculate the superposed position of the instrument on the 2D image, and wherein determining further includes compensating for a breathing-induced movement of a given body part within the body volume of interest based on a measured breathing position using a movement model of the body part; and
g) a means for superimposing the determined position of the instrument with the selected stored 2D image.

11. The instrument tracking system of claim 10, further comprising at least one reference probe positioned on at least one of (i) the means for generating 2D images and (ii) the body.

* * * * *